(12) United States Patent
Johnson et al.

(10) Patent No.: US 11,937,829 B2
(45) Date of Patent: Mar. 26, 2024

(54) TOURNIQUET WITH ROTATABLE BUCKLE ASSEMBLY

(71) Applicant: Tactical Medical Solutions, LLC, Anderson, SC (US)

(72) Inventors: Ross A. Johnson, Anderson, SC (US); Richard A. Hester, Greenville, SC (US)

(73) Assignee: Tactical Medical Solutions, LLC, Anderson, SC (US)

( * ) Notice: Subject to any disclaimer, the term of this patent is extended or adjusted under 35 U.S.C. 154(b) by 981 days.

(21) Appl. No.: 16/579,175

(22) Filed: Sep. 23, 2019

(65) Prior Publication Data

US 2020/0015828 A1 Jan. 16, 2020

Related U.S. Application Data

(63) Continuation of application No. 16/496,611, filed as application No. PCT/US2018/024126 on Mar. 23, 2018.

(Continued)

(51) Int. Cl.
*A61B 17/132* (2006.01)
*A44B 11/00* (2006.01)
(Continued)

(52) U.S. Cl.
CPC ........ *A61B 17/1325* (2013.01); *A44B 11/005* (2013.01); *A44B 11/006* (2013.01);
(Continued)

(58) Field of Classification Search
CPC .. A61B 17/132–1327; A61B 11/02–14; A61B 11/28; A61B 11/2538; A61B 11/2542
See application file for complete search history.

(56) References Cited

U.S. PATENT DOCUMENTS

| 462,547 | A | 11/1891 | Gintzburg et al. |
| 496,630 | A | 5/1893 | Adams |

(Continued)

FOREIGN PATENT DOCUMENTS

| CA | 1274971 A | 10/1990 |
| CA | 2534716 A1 | 8/2006 |

(Continued)

OTHER PUBLICATIONS

Calkins, Mark D. MD et al., Evaluation of Possible Tourniquet Systems For the Far Forward Setting, Washington Headquarters Services, Directorate for Information Operations and Reports, Jan. 20, 1999, pp. 1-38, Walter Reed Army Institute of Research, Division of Surgery, Combat Trauma Research, Washington DC.

(Continued)

*Primary Examiner* — Eduardo C Robert
*Assistant Examiner* — Steven J Cotroneo
(74) *Attorney, Agent, or Firm* — CAHN & SAMUELS, LLP

(57) ABSTRACT

The present invention relates generally to first aid articles and more specifically tourniquets suitable for one handed application. One embodiment of the invention is directed to a tourniquet having a base defining first and second ends. A constricting band is attached to and extends from the first end of the base. A windlass handle is engaged with the constricting band. The constricting band is threaded through a self cinching stepped buckle. A buckle connector includes a hook member that engages the stepped buckle and is partly held in place through urging against a loop of the constriction band.

14 Claims, 6 Drawing Sheets

Related U.S. Application Data

(60) Provisional application No. 62/475,854, filed on Mar. 23, 2017.

(51) Int. Cl.
*A44B 11/06* (2006.01)
*A44B 11/12* (2006.01)
*A44B 11/18* (2006.01)
*A44B 11/28* (2006.01)
*A61B 17/00* (2006.01)

(52) U.S. Cl.
CPC ............ *A44B 11/06* (2013.01); *A44B 11/125* (2013.01); *A44B 11/18* (2013.01); *A44B 11/28* (2013.01); *A61B 2017/00477* (2013.01); *Y10T 24/3404* (2015.01); *Y10T 24/3405* (2015.01); *Y10T 24/4081* (2015.01)

(56) References Cited

U.S. PATENT DOCUMENTS

| | | | |
|---|---|---|---|
| 611,794 A | 10/1898 | Ross | |
| 818,292 A | 4/1906 | Reid | |
| 1,416,417 A | 5/1922 | Robinson | |
| 1,419,592 A | 6/1922 | Sturges | |
| 1,708,985 A | 1/1928 | Wadsworth | |
| 1,887,096 A | 2/1932 | Hodge | |
| 1,855,482 A | 4/1932 | McArthur | |
| 2,037,558 A | 4/1936 | Anderson | |
| 2,084,412 A | 6/1937 | Schaefer | |
| 2,250,977 A | 7/1941 | Walker | |
| RE21,948 E | 11/1941 | White et al. | |
| 2,387,428 A | 10/1945 | Brothers | |
| 2,403,712 A | 7/1946 | Elwell | |
| 2,480,430 A | 9/1949 | Walters | |
| D185,635 S | 7/1959 | Gerlach | |
| 3,404,436 A | 10/1968 | McMurray | |
| D260,074 S | 8/1981 | Lewis | |
| 4,549,550 A | 10/1985 | Kami et al. | |
| 4,551,889 A | 11/1985 | Narayan et al. | |
| 4,608,735 A | 9/1986 | Kasai | |
| 4,610,056 A * | 9/1986 | Emmert | A44B 11/12 24/198 |
| 4,778,033 A * | 10/1988 | Gonzalez | A44B 11/00 D29/124 |
| 4,794,656 A | 6/1989 | Henley, Jr. | |
| D324,328 S | 3/1992 | Pagan | |
| 5,607,448 A | 3/1997 | Stahl et al. | |
| D385,178 S | 10/1997 | Poulin | |
| 5,993,362 A | 11/1999 | Ghobadi | |
| 6,298,521 B1 | 10/2001 | Butterfield | |
| 6,540,707 B1 | 4/2003 | Stark et al. | |
| 6,544,188 B1 | 4/2003 | Chesney et al. | |
| 6,602,214 B2 | 8/2003 | Heniz et al. | |
| 6,746,470 B2 | 6/2004 | McEwen et al. | |
| 6,884,254 B2 | 4/2005 | Brooks | |
| 6,899,720 B1 * | 5/2005 | McMillan | A61B 17/1322 606/203 |
| D516,901 S | 3/2006 | Murray | |
| D527,981 S | 9/2006 | Sato | |
| D545,663 S | 7/2007 | Sato | |
| 7,296,327 B2 | 11/2007 | Anderson et al. | |
| 7,353,573 B2 | 4/2008 | Anscher | |
| D592,484 S | 5/2009 | Ricereto | |
| 7,582,102 B2 | 9/2009 | Heniz et al. | |
| 7,752,722 B2 | 7/2010 | Calkin | |
| 7,776,064 B2 | 8/2010 | Jennifer et al. | |
| 7,842,067 B2 | 11/2010 | Esposito | |
| 7,892,253 B2 * | 2/2011 | Esposito | A61B 17/1327 606/203 |
| D649,642 S | 11/2011 | Johnson | |
| 8,065,781 B2 | 11/2011 | Chao | |
| 8,214,975 B2 | 7/2012 | Calkin | |
| 8,303,620 B2 | 11/2012 | Johnson et al. | |
| 8,348,970 B2 | 1/2013 | Janota | |
| 8,776,323 B2 * | 7/2014 | McLennan | B60P 7/0823 410/97 |
| 11,466,753 B2 * | 10/2022 | Farrell | A62B 35/0025 |
| 2002/0148461 A1 | 10/2002 | Heinz et al. | |
| 2003/0028215 A1 * | 2/2003 | Brooks | A61B 17/1327 606/203 |
| 2003/0139766 A1 | 7/2003 | McEwen et al. | |
| 2005/0049630 A1 | 3/2005 | Ambach | |
| 2005/0049830 A1 | 3/2005 | Kouzitzin | |
| 2005/0113866 A1 | 5/2005 | Heinz et al. | |
| 2005/0240217 A1 * | 10/2005 | Jennifer | A61B 17/1322 606/203 |
| 2005/0267518 A1 | 12/2005 | Wright | |
| 2005/0273134 A1 | 12/2005 | Esposito | |
| 2006/0095072 A1 | 5/2006 | TenBrink | |
| 2006/0185131 A1 * | 8/2006 | Anderson | A44B 11/006 24/171 |
| 2007/0005107 A1 | 1/2007 | Janota | |
| 2008/0148533 A1 | 6/2008 | Calkin | |
| 2008/0183207 A1 * | 7/2008 | Horne | A61B 17/1327 606/203 |
| 2008/0221612 A1 | 9/2008 | Rose | |
| 2009/0006284 A1 | 1/2009 | Liu et al. | |
| 2009/0024159 A1 | 1/2009 | Nee et al. | |
| 2009/0151132 A1 | 6/2009 | Rotunno, Jr. | |
| 2010/0057120 A1 * | 3/2010 | Kirkham | A61B 17/1322 606/203 |
| 2010/0137900 A1 | 6/2010 | Chao | |
| 2010/0234877 A1 | 9/2010 | Pienkowski et al. | |
| 2010/0263680 A1 | 10/2010 | Calkin | |
| 2011/0178546 A1 | 7/2011 | Johnson et al. | |
| 2011/0270299 A1 | 11/2011 | Rose et al. | |
| 2011/0307004 A1 * | 12/2011 | Johnson | A61B 17/1322 606/203 |

FOREIGN PATENT DOCUMENTS

| | | |
|---|---|---|
| CA | 2542058 C | 6/2014 |
| CN | 2467055 Y | 12/2001 |
| CN | 201375542 Y | 1/2010 |
| CN | 201441415 U | 4/2010 |
| CN | 202497191 U | 10/2012 |
| CN | 202505426 U | 10/2012 |
| CN | 205102076 U | 3/2016 |
| DE | 3417998 A1 | 12/1984 |
| DE | 3327528 A1 | 2/1985 |
| EP | 1692958 A1 | 8/2006 |
| ES | 296362 Y | 8/1987 |
| FR | 2548009 A1 | 1/1985 |
| GB | 572460 A | 10/1945 |
| GB | 674631 A | 6/1952 |
| GB | 2138490 A | 10/1984 |
| GB | 2141344 A | 12/1984 |
| GB | 2179392 A | 3/1987 |
| JP | 2007508047 A | 4/2007 |
| MX | 163385 B | 5/1992 |
| WO | 9842257 A1 | 10/1998 |
| WO | 2005053506 A2 | 6/2005 |
| WO | 2005090207 A1 | 9/2005 |
| WO | 2005053506 A3 | 3/2006 |
| WO | 2011072126 A2 | 6/2011 |

OTHER PUBLICATIONS

McEwen, James A. Ph.D et al., Surgical Tourniquet Technology Adapted for Military and Prehospital Use, pp. 1-12, Vancouver, Canada.

European Patent Office, Espacenet, English Abstract of CN2467055Y, retrieved Sep. 24, 2020.

European Patent Office, Espacenet, English Abstract of CN201375542Y, retrieved Sep. 24, 2020.

European Patent Office, Espacenet, English Abstract of CN201441415U, retrieved Sep. 24, 2020.

European Patent Office, Espacenet, English Abstract of CN202497191U, retrieved Sep. 24, 2020.

(56) References Cited

OTHER PUBLICATIONS

European Patent Office, Espacenet, English Abstract of CN202505426U, retrieved Sep. 24, 2020.
European Patent Office, Espacenet, English Abstract of CN205102076U, retrieved Sep. 24, 2020.
European Patent Office, Espacenet, English Abstract of DE3327528A1, retrieved Sep. 24, 2020.
European Patent Office, Espacenet, English Abstract of DE3417998A1, retrieved Sep. 24, 2020.
European Patent Office, Espacenet, English Abstract of JP2007508047A, retrieved Sep. 24, 2020.
European Patent Office, English Abstract of EP1670366A0, retrieved Sep. 25, 2020.
European Patent Office, Espacenet, English Abstract of CA2534716C, retrieved Sep. 24, 2020.
European Patent Office, Examination Report for 18771970.3, dated Aug. 30, 2021.
European Patent Office, Extended Search Report for PCT/US2018024125, dated Dec. 2, 2020.
Japan Patent Office, Notice of Rejection for 2020-501433, dated Jan. 31, 2022.
Japan Patent Office, English Translation of Notice of Rejection for 2020-501433, retrieved Oct. 17, 2022.

\* cited by examiner

TOURNIQUET WITH ROTATABLE BUCKLE ASSEMBLY

This application is a continuation application of U.S. patent application Ser. No. 16/496,611, filed Sep. 23, 2019, which is a national stage application from PCT Application No. PCT/US2018/024126, filed on Mar. 23, 2018, which claims the benefit of U.S. Provisional Patent Application No. 62/475,854 filed on Mar. 23, 2017, which are incorporated herein by reference in their entireties.

I. FIELD OF THE INVENTION

This invention relates to tourniquets suitable for one-handed application.

II. BACKGROUND OF THE INVENTION

Uncontrolled hemorrhage from trauma remains a major cause of death, both on the battlefield and in civilian situations. Untreated, extreme bleeding as in the case of arterial bleeding can cause hypovolemic shock within just minutes.

Tourniquets are well-known devices used to stop blood loss from trauma. When properly deployed, they provide life-saving support in emergency situations when an injured victim is alone or cannot reach immediate medical attention. A standard tourniquet is a tightly tied or wound band applied around an injured limb in an attempt to increase pressure around the limb, above the injury and stop severe bleeding or uncontrolled hemorrhaging. Rapid application of a tourniquet above the site of injury is paramount to effective hemorrhage control, as is rapid incremental release of a tourniquet once medical assistance is available to provide next-step trauma management.

In emergency situations when the injured victim is alone, he or she must be able to apply the tourniquet to his or her own injured body part to occlude blood flow. Tourniquet self-application is especially challenging when the victim is constrained to using only one hand. With limited dexterity, the victim may have to undergo one-handed tightening or adjusting of the tourniquet occur at unusual angles.

The present invention relates to an improved tourniquet particularly suited for medics trained or skilled in tourniquet application. Developments in tourniquet design, including tourniquets designed for one-handed application, have become available in recent years. Many such tourniquets are of the "windlass" type. Such tourniquets typically include a strap threaded through a windlass handle and coupled to a tourniquet base. In order to tighten the tourniquet around a limb, the strap is threaded through a buckle and the windlass handle is twisted thereby causing the strap to constrict circumferentially about the limb. A drawback to some of these known tourniquets is, under certain circumstances, they do not facilitate speedy deployment to trapped limbs. In order to deploy these tourniquets to trapped limbs, the strap must be manually unthreaded from the buckle and subsequently routed around the limb and rethreaded with the buckle before being tightened. That process requires acute concentration as well as precise dexterity, characteristics that are often not available to a victim in crisis or a first responder in a high stress environment. In addition, that process delays tourniquet application where even a few seconds of delay can cause fatal blood loss.

Another shortcoming of some known tourniquets designed for one-handed application is that they are sometimes difficult to cinch even when the strap is engaged with the buckle requiring several tugs on the strap and sometimes aid of a second hand. Often, it necessary for a victim to apply the tourniquet to its own limb. The victim has typically suffered severe trauma and may not have the presence of mind, the patience or the stamina to overcome cinching difficulties.

Still further, at least some existing tourniquets delay one-handed release after use. Because tourniquets are designed to occlude blood flow in emergency situations, conventional tourniquets delay one-handed release of the tourniquet buckle in order to prevent inadvertent disengagement. However, rapid incremental release of a tourniquet can be life-saving when trained tourniquet users must adjust the position and/or location of the tourniquet or when next-step trauma management is available and necessary.

For example, certain tourniquet buckle designs are comprised of components that may cause friction between interfacing buckle components. Such friction prevents the inadvertent release of the buckle but disadvantageously slows down the rapid release of the buckle when needed. Additionally, friction between tourniquet buckle components may cause wear with repeated use.

Known tourniquets also restrict the rotational capability of buckle components once the buckle is engaged. For military personnel, law enforcement personnel, first responders, emergency medical personnel, and others who are trained or skilled in proper tourniquet application, tightening of a tourniquet from a precise angle can facilitate restriction of blood flow from areas that are especially difficult to occlude, such as limbs of larger circumferences like the proximal or distal thigh region. The rotation of one or more buckle components within an engaged tourniquet buckle can in some instances enable a more targeted, angled pull of a tourniquet strap to tighten.

Accordingly, there is a need for a lightweight, low profile, low cost tourniquet that can be rapidly self-applied and released by a trained user with one hand and adjusted to a targeted angle of tightening.

III. BRIEF SUMMARY OF THE INVENTION

It is an object of the present invention to provide a tourniquet having a buckle that facilitates one handed tourniquet application.

It is a further object of the invention to provide a tourniquet buckle that minimizes time and effort to secure the buckle into an adjustable, secured position.

It is a further object of the invention to provide a tourniquet buckle that permits transverse rotation of the buckle while engaged in its secured position of up to about 45 degrees.

It is another object of the invention to provide a tourniquet buckle that minimizes unintended detachment of the buckle.

It is another object of the invention to provide a tourniquet buckle that facilitates rapid, release of the buckle when intended.

It is yet another object of the invention to provide a tourniquet buckle that maximizes tolerances permissible in the manufacturing process of the tourniquet buckle.

In accordance with an embodiment of the invention, a tourniquet comprises a base having first and second ends. A constricting band is attached to and extends from the first end of the base. A windlass handle is engaged with the constricting band. A tourniquet buckle assembly is further provided. The tourniquet buckle assembly includes a substantially rectangular stepped buckle frame including a frame member and a step member. A a self-cinching sliding arm transversely extends from a first side of the substantially rectangular stepped buckle frame to a second opposing side of the substantially rectangular stepped buckle frame. The sliding arm is configured to slide along the buckle frame. A buckle connector, including a hook member is configured to engage the stepped buckle frame and a strap channel base member. The strap channel base member is integrally formed with the hook member, and the strap channel base member includes a central aperture. A loop threaded through the central aperture of said strap channel base member and disposed in a trough of said hook member wherein said step member is adjustably secured in the trough of said hook member and maintained in its engaged position by contacting at least one of said loop and an inner surface of said hook member. A loop is threaded through the central aperture of the strap channel base member and disposed in a trough of the hook member such that the step member is adjustably secured in the trough of the hook member and maintained in an engaged position by contacting at least one of the loop and an inner surface of the hook member.

As used herein "substantially," "generally," "approximately," "about" and other words of degree are relative modifiers intended to indicated permissible variation from the characteristic so modified. It is not intended to be limited to the absolute value or characteristic which it modifies but rather possessing more of the physical or functional characteristic than its opposite, and preferably, approaching or approximating such a physical or functional characteristic.

IV. BRIEF DESCRIPTION OF THE DRAWINGS

Some embodiments of the present invention are illustrated as an example in the accompanying drawings and are described in sufficient detail to enable those skilled in the art to practice the invention. It is to be understood that other embodiments may be utilized and that structural changes based on presently known structural and/or functional equivalents may be made without departing from the scope of invention. The above and other objects, advantage and features of the present invention will be more readily apparent when read in conjunction with the following drawings wherein.

V. DETAILED DESCRIPTION OF THE INVENTION

A description of various embodiments of the invention follows.

Figure 1:
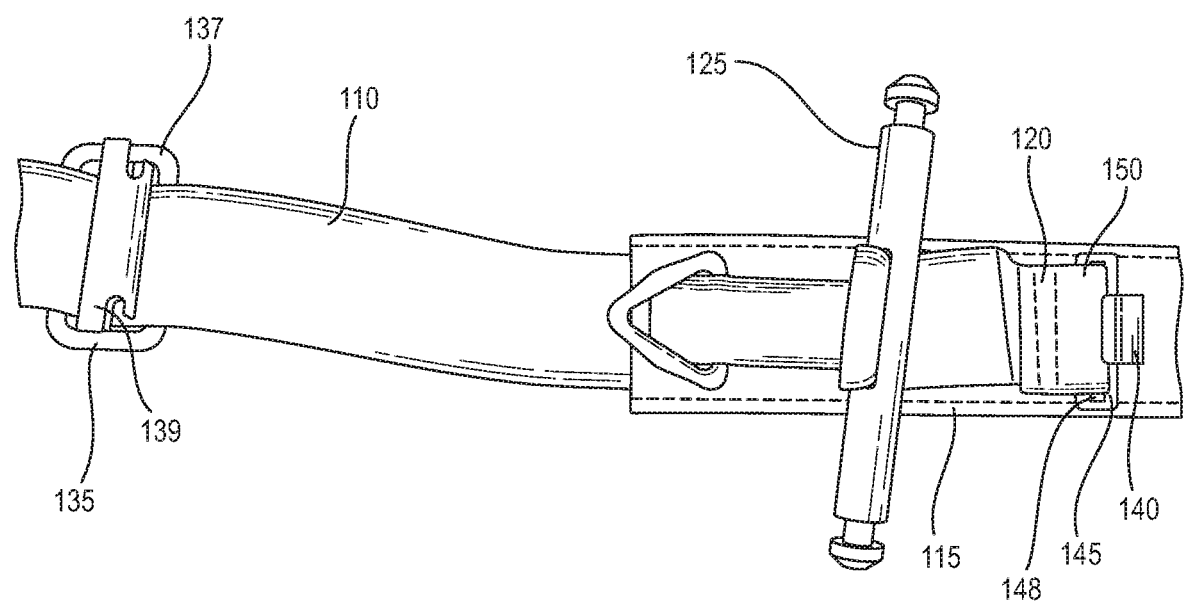
FIG. 1 depicts a top view of a tourniquet with a disengaged buckle in accordance with an embodiment of the invention.
Figure 2:
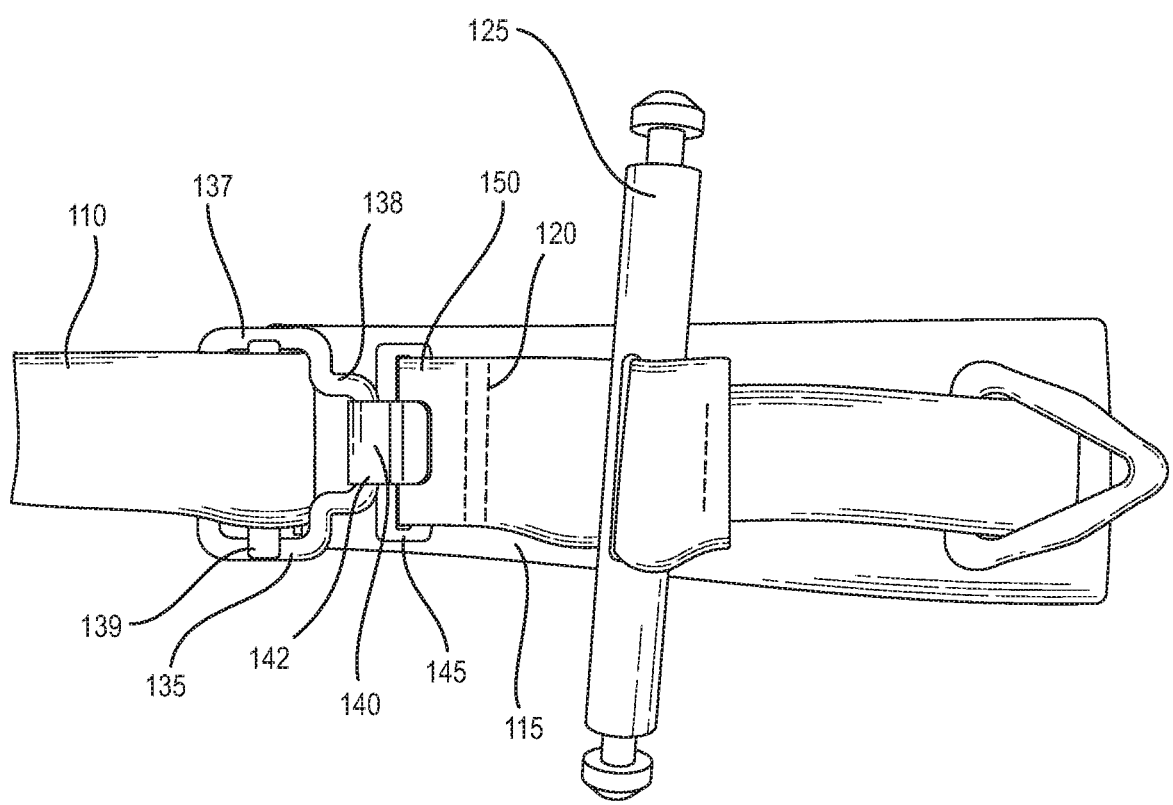
FIG. 2 depicts a top view of a tourniquet with an engaged buckle in accordance with an embodiment of the invention.
Figure 3:
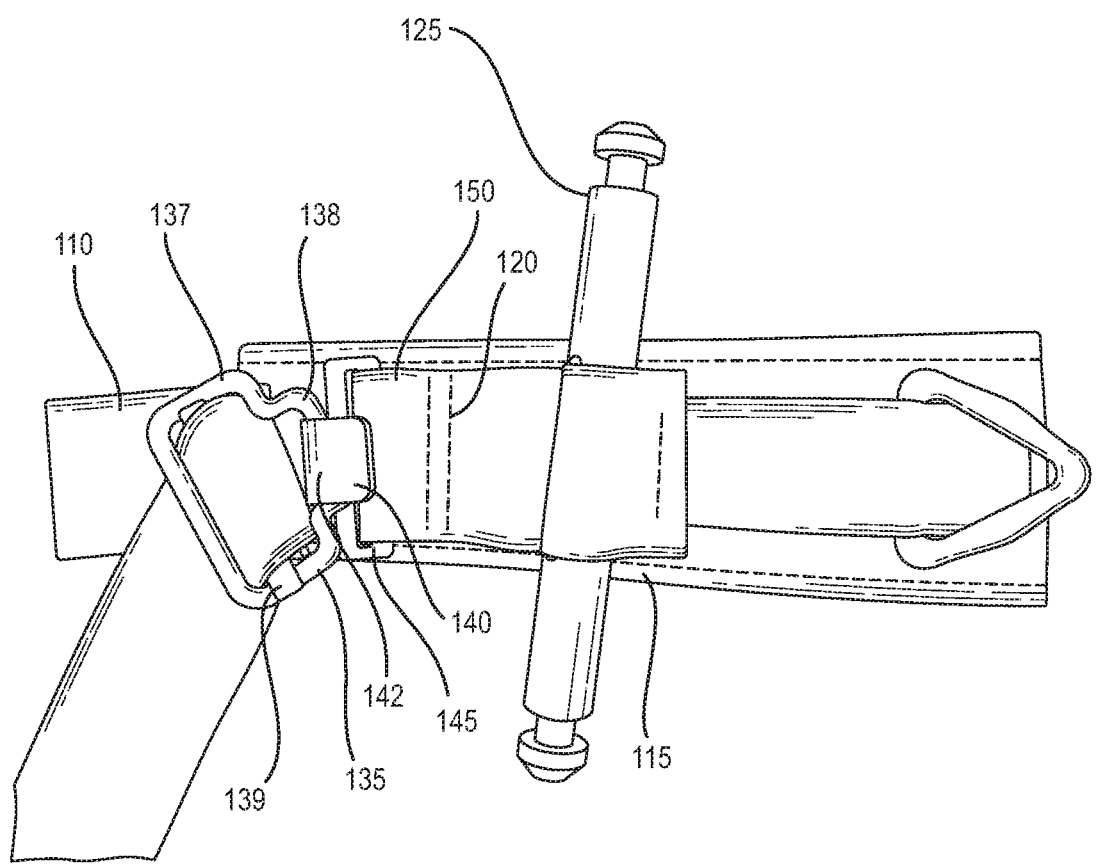
FIG. 3 depicts a top view of a tourniquet with an engaged and rotated buckle in accordance with an embodiment of the invention.

Referring now to FIGS. 1-3, a tourniquet 101 according to the invention includes a constricting band 110 engaged with a base 115. Constricting band 110 preferably has a width of between about 1 inch and about 3 inches, and more preferably a width of between about 1 inch and about 2 inches. In an exemplary embodiment, the constricting band has a width of about 1.5 inches.

A first end of the tourniquet 110 is fixedly attached, e.g., stitched, to base 115 at an attachment point 120. Constricting band 110 is then threaded through and/or engaged with a tourniquet handle 125 and reengaged with the base 115 at a second end of base 115. Constricting band 110 then extends from the second end of the base 115 by at least a sufficient distance to allow the strap to be wrapped around the limb of an average size adult male. In some embodiments, tourniquet handle may be attached to the base 115 in the manner described in U.S. Pat. No. 7,776,064 which is herein incorporated by reference.

In accordance with the invention, an exemplary embodiment of the tourniquet according to this invention further includes a buckle assembly 130 comprising a self-cinching, rotatable buckle 135 and a buckle connector 140. As illustrated in FIGS. 1-5 and FIG. 9, in some embodiments buckle 135 includes a frame member 137 having a self-cinching slide member 139 engaged with frame member 137. In some embodiments, the self-cinching slide member 139 comprises a structural member such as a cuff or bar that extends across an opening of the frame member 137 and forms a tongue and groove type engagement with first and second opposing sides 137A and 137B, respectively, of frame member 137. As shown in FIGS. 1-5, constricting band 110 is looped over the self-cinching slide member 139 such that by simply pulling the free end of constricting band 110, the self-cinching slide member 139 slides along frame member 137 until constricting band 110 is pinched between self-cinching slide member 139 and side 137a and/or side 137b of the frame member 137.

As illustrated in FIGS. 4-6 and 9, stepped rectangular buckle 135 comprises a step member 138 and a frame member 137. In an exemplary embodiment, frame member 137 comprises three sides of a rectangle, i.e. a base 137C and two sides, 137A and 137B. Step member 138 protrudes from frame member 137 and comprises a raised step edge 138A, two side supports 138B and 138C, and two flared base portions 138D and 138E. The raised step edge 138A extends substantially parallel to base 137C. Side supports 138B and 138C are integrally formed with raised edge 138A at approximately perpendicular corners and extend rearwardly towards base 137C. Base portions 138D and 138E of step member 138 extend outwardly from the two side supports 138B and 138C and are integrally formed with sides 137A and 137B at substantially right angles. The raised edge 138A has a length that is slightly greater than the width W1 of hook member 142 and less than the length of frame member base 137C. In some embodiments, buckle 135 has rounded rectangular corners. In accordance with FIG. 6, in some embodiments buckle 135 is cylindrical in cross section. The cross sectional shape is believed to minimize the level of friction between step member 138 and hook member 142 and allow an individual to set step member 138 into its engaged position in the crescent trough of buckle connector 140 with greater ease.

In accordance with another aspect of the invention, buckle connector 140 is pivotally attached to base 115 proximate to the first end of base 115. As illustrated further in FIG. 7, buckle connector 140 comprises a hook member 142 and a strap channel base member 145. Hook member 142 comprises a cuff having an interior surface. The hook member 142 extends from a strap channel base member 145 which defines a strap engaging aperture 148. The strap channel base member 145, as further illustrated in FIG. 7, preferably has rounded edges and includes a first substantially vertical side 145A from which hook member 142 extends and a second side 145B which is slightly curved.

Figure 4:
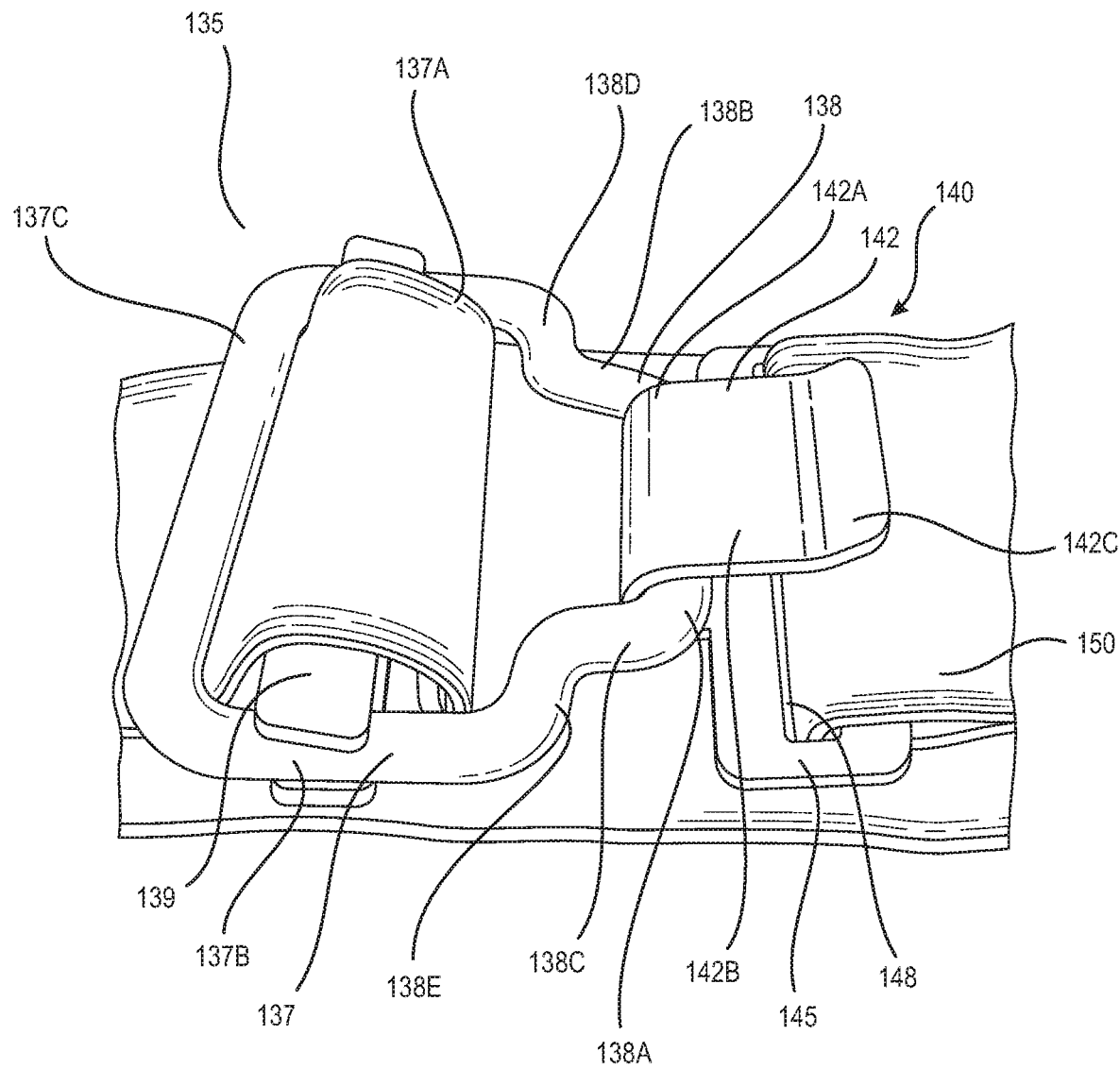
FIG. 4 depicts a side view of the buckle assembly in accordance with an embodiment of the invention.
Figure 5:
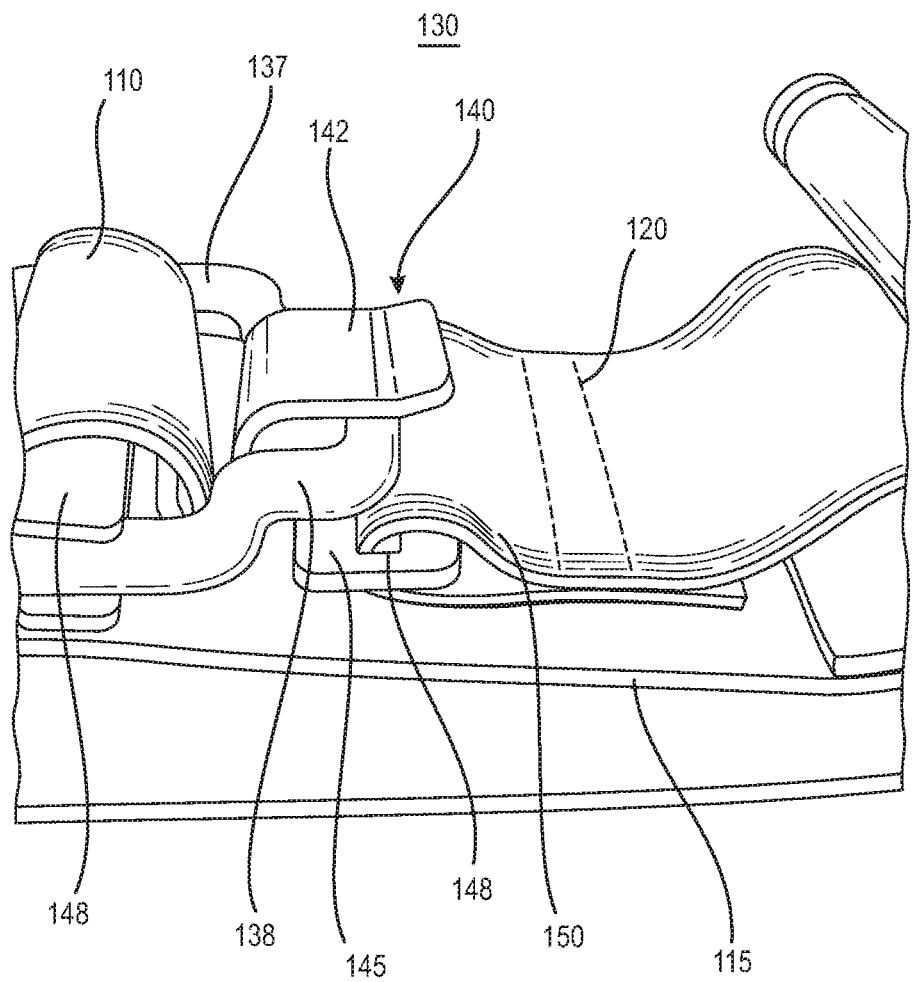
FIG. 5 depicts a side view of the buckle assembly in accordance with another embodiment of the invention.
Figure 6:
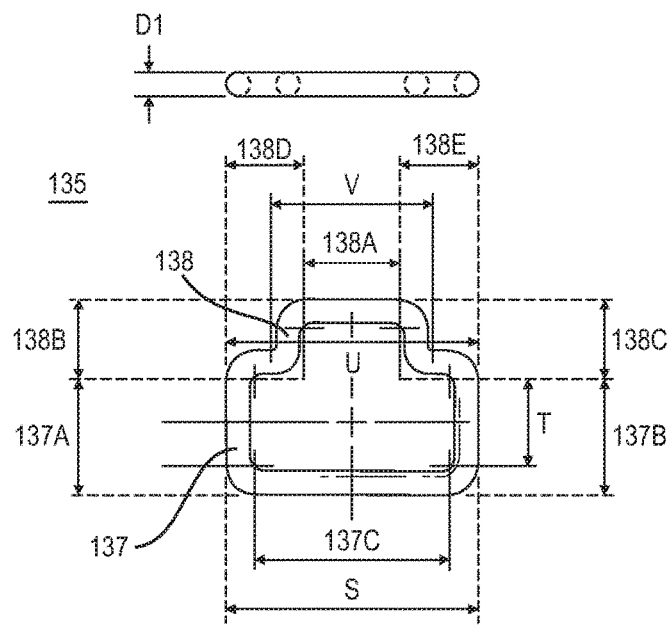
FIG. 6 depicts a top view of a buckle in accordance with an embodiment of the invention.

As illustrated in FIGS. 2-5, buckle connector 140 is connected to base 115 by a loop 150 formed near the first end of constricting band 110 and is constructed to form a friction fit with buckle 135 and loop 150. In some embodiments, constricting band 110 comprises material sufficiently flexible to create a circumferential band while accepting a mechanical advantage mechanism. In some embodiments constricting band 110 is made of heavy weight polypropylene webbing or nylon webbing. In an exemplary embodiment, loop 150 is comprised of the identical material as constricting band 110. It is desirable to keep buckle connector 140 engaged with buckle 135 unless and until a user actively disengages them. It is also desirable for buckle 135 to be capable of adjustment and/or rotation while engaged with buckle connector 140 to facilitate targeted, angled tightening of the constricting band 110. Further, it is beneficial for buckle 135 to rapidly disengage from buckle connector 140 after use. In accordance with an aspect of the invention, as illustrated in FIGS. 4-5, step member 138 is adjustably secured in the crescent trough of of hook member 142 and maintained in its engaged position by contact with loop 150 and/or the inner surface of hook member 142. Loop 150 acts as a barrier to inadvertent disengagement of buckle 135 as well as a means for attaching buckle connector 140 to base 115. With step member 138 engaged with buckle connector 140, buckle 135 is capable of a certain degree of rotation relative to buckle connector 140. Rotation beyond a certain degree of transverse and longitudinal rotation is believed to be thwarted by loop 150 catching buckle 135 and/or by hook member 142 urging against the portion of constriction band 110 which is looped over self-cinching member 139. Likewise, buckle connector 140 may realize such rotation relative to buckle 135. FIG. 3 illustrates an exemplary embodiment of the tourniquet with buckle 135 in a rotated position when engaged with buckle connector 140. In some embodiments, buckle 135 is capable of transverse rotation of up to about 45 degrees when engaged with buckle connector 140. In another embodiment, buckle 135 is capable of longitudinal rotation of up to about 180 degrees when engaged with buckle connector 140.

Figure 7:
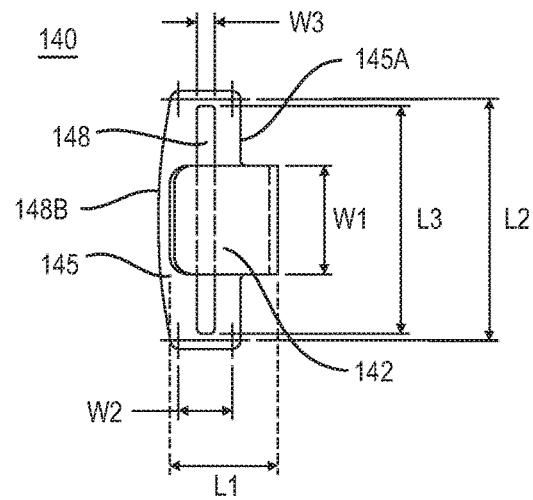
FIG. 7 depicts a top view of a buckle connector in accordance with an embodiment of the invention.

As illustrated in FIGS. 4-5 and 7, buckle connector 140 comprises a cuff. Hook member 142 has a lengthwise dimension L1 and a width W1. In keeping with an aspect of the invention, hook member 142 has a width W1 that is substantially smaller than the length of buckle frame base 137C. In one embodiment, W1 is one half the length of 137C. Because the size of the opening of frame member 135 is larger than the length of hook member 142, it is easier for an individual under stress to connect buckle connector 140 to buckle 135 as it minimizes complicated motor movements and reduces the level of hand eye coordination required to connect buckle connector 140 to buckle 135. These are particularly important considerations in low light, high stress combat environments.

Figure 8:
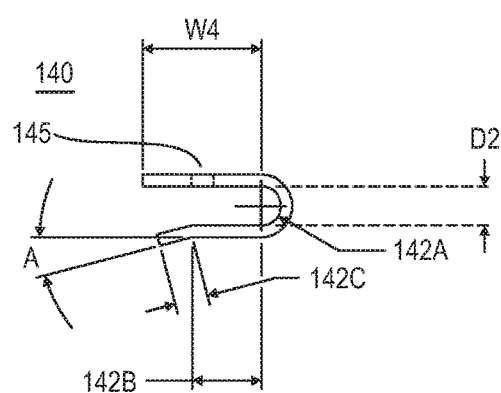
FIG. 8 depicts a side view of the buckle connector in accordance with an embodiment of the invention.
Figure 9:
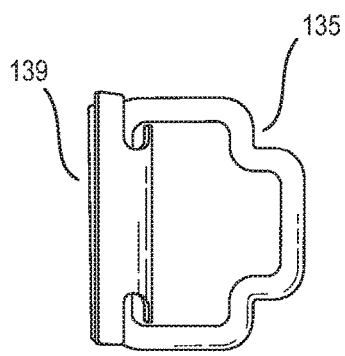
FIG. 9 depicts a top view of a tourniquet buckle with self-cinching slide member in accordance with an embodiment of the invention.

As illustrated in FIG. 8, hook member 142 is integrally formed with strap channel base member 145. Hook member 142 is generally J shaped and includes a trough 142A, a leg 142B, and an end portion 142C integrally formed with leg 142B. End portion 142C is offset from the axis of 142B by an angle "A" of about 15 degrees. This offset end portion functions as a ramp and facilitates insertion of step edge 138A into trough 142A of hook member 142.

In keeping with another aspect of the invention, it is desirable to minimize the loosening of the tourniquet such as may happen, e.g., if the tourniquet is snagged during patient movement. Accordingly, a loop 150 is threaded through eyelet 148 and fixedly attached to base 115, e.g., by stitching, to connect buckle connector 140 to base 115. When step member 138 is lodged in the crescent trough of buckle connector 140, as the tourniquet is displaced during patient movement or tactical extraction, buckle connector 140 is inclined to pivot about loop 150 and is disinclined to pivot about buckle 135 which minimizes the prospect of accidental loosening of constriction band 110.

The following Example illustrates an exemplary embodiment of a tourniquet buckle of the present invention.

EXAMPLE

A tourniquet of the type shown in FIGS. 1-9 has a buckle 135 and a buckle connector 140 made from metal. In this example, the buckle 135 has a cylindrical diameter D1 of approximately 0.187". The buckle 135 has a step member 138 and a frame member 137. The frame member 137 comprises three sides of a rounded rectangle with a base length 137C measuring approximately 1.5" excluding the rounded corners and extended length S including the abutting rounded corners and measuring approximately 2.0". Sides 137A and 137B each measure approximately 0.937" including one rounded corner and have a truncated width T excluding rounded corners that measures approximately 0.688". Step member 138 has a total length U about equal to the frame extended base length S or approximately 2.0". Raised edge 138A is centered in the buckle frame such that the center of raised edge 138A is approximately 0.750" or about halfway in from frame base 137C. The raised stepped edge 138A has a length of about 0.760" excluding its surrounding rounded corners and an extended length V including rounded corners measuring approximately 1.258". The depth of the step member 138 is approximately equal in length to sides 138B and 138C and measures approximately 0.654" included the rounded corners. The flared step base portions 138D and 138E each have a length of approximately 0.619" including rounded corners.

In this example, the buckle connector 140 has a hook member 142 and strap channel bar 148. As illustrated in FIG. 7, hook member 142 has a width W1 of approximately 0.750". Strap channel bar has a vertical length L2 of approximately 1.640" excluding its rounded edges and a width W2 of approximately 0.365" excluding its rounded edges. Strap channel bar 148 has a generally rounded rectangular aperature that is approximately centered in bar 148 and has a length L3 of approximately 1.562" and a width W3 of approximately 0.125".

As shown in FIG. 8, hook member 142 is a generally J-shaped structure integrally formed with strap channel base member 145. Strap channel base member 145 has a width W4 of approximately 0.64". Hook member 142 has a generally hemispherical trough with a diameter D2 of about 0.336" and leg 142B with a length measuring about 0.389". Integrally formed with leg 142B is end portion 142C, which has a length of about 0.163" and is offset from the axis of leg 142B by an angle of up to about 15 degrees.

While the present invention has been illustrated and described by means of specific embodiments and alternatives, it is to be understood that numerous changes and modifications can be made without departing from the spirit and scope of the invention. Therefore, it should be understood that the invention is not to be limited in any way except in accordance with the appended claims and their equivalents.

What is claimed is:

1. A tourniquet comprising:
    a base having first and second ends;
    a constricting band attached to and extending from the first end of said base;
    a windlass handle engaged with said constricting band;
    a tourniquet buckle assembly comprising:
        a substantially rectangular stepped buckle frame including a frame member and a step member,
        a self-cinching sliding arm transversely extending from a first side of said substantially rectangular stepped buckle frame to a second opposing side of said substantially rectangular stepped buckle frame, said sliding arm being configured to slide along the buckle frame;
        a buckle connector, including a hook member configured to engage said stepped buckle frame and a strap channel base member, said strap channel base member integrally formed with said hook member and said strap channel base member including a central aperture; and
    a loop threaded through the central aperture of said strap channel base member and disposed in a trough of said hook member wherein said step member is adjustably secured in the trough of said hook member and maintained in its engaged position by contacting at least one of said loop and an inner surface of said hook member.

2. The tourniquet of claim 1, wherein said buckle frame has a cylindrical cross section.

3. The tourniquet of any of claim 2, wherein said self-cinching sliding arm forms a tongue and groove type engagement with said buckle frame.

4. The tourniquet of claim 3, wherein said hook is pivotally attached to said loop.

5. The tourniquet of claim 3, wherein said loop is a substantially resilient textile material.

6. The tourniquet of claim 3, wherein said hook and said loop are configured to form a friction fit with said buckle frame.

7. The tourniquet of claim 3, wherein said buckle frame is capable of transverse rotation up to 45 degrees when engaged with said hook member.

8. The tourniquet of claim 7, wherein said buckle frame is capable of longitudinal rotation up to 180 degrees when engaged with said quick connect and release hook.

9. The tourniquet of claim 8, wherein said step member of said buckle frame has a length that is slightly greater than a width of said hook member.

10. The tourniquet of claim 8, wherein said hook member has a width that is about half of the lengthwise dimension of a base of said frame member.

11. The tourniquet of claim 3, wherein said hook is pivotally attached to said loop.

12. The tourniquet of claim 11, wherein said loop is a substantially resilient textile material.

13. The tourniquet of claim 1, wherein said buckle frame is capable of transverse rotation up to 45 degrees when engaged with said hook member.

14. The tourniquet of claim 13, wherein said buckle frame is capable of longitudinal rotation up to 180 degrees when engaged with said hook member.

* * * * *